(12) United States Patent
Pedersen et al.

(10) Patent No.: US 7,517,339 B2
(45) Date of Patent: *Apr. 14, 2009

(54) PEELABLE AND FLUSHABLE OSTOMY POUCH AND METHOD OF USE

(75) Inventors: Ole Pedersen, Brøndby (DK); Jørgen Forbjerg-Iarsen, Skaevinge (DK); Claudio Giori, Riverwoods, IL (US)

(73) Assignee: Hollister Incorporated, Libertyville, IL (US)

( * ) Notice: Subject to any disclaimer, the term of this patent is extended or adjusted under 35 U.S.C. 154(b) by 53 days.

This patent is subject to a terminal disclaimer.

(21) Appl. No.: 10/969,523

(22) Filed: Oct. 20, 2004

(65) Prior Publication Data

US 2005/0113770 A1 May 26, 2005

Related U.S. Application Data

(60) Provisional application No. 60/512,760, filed on Oct. 21, 2003.

(30) Foreign Application Priority Data

Oct. 21, 2003 (DK) .................. 2003 01549

(51) Int. Cl.
*A61F 5/449* (2006.01)
(52) U.S. Cl. ..................... 604/345; 604/344
(58) Field of Classification Search .......... 604/344, 604/345, 327, 332
See application file for complete search history.

(56) References Cited

U.S. PATENT DOCUMENTS

| 2,778,362 | A | * | 1/1957 | Pollock et al. ............. 604/345 |
| 3,089,493 | A | * | 5/1963 | Galindo ..................... 604/342 |
| 3,934,587 | A | | 1/1976 | Gordon |
| 4,213,458 | A | | 7/1980 | Nolan et al. |
| 4,372,308 | A | | 2/1983 | Steer et al. |
| 4,372,311 | A | | 2/1983 | Potts ........................ 604/364 |
| 4,419,100 | A | * | 12/1983 | Alexander ................ 604/339 |
| 4,439,191 | A | * | 3/1984 | Hogan ...................... 604/332 |
| 4,518,087 | A | * | 5/1985 | Goglio ...................... 383/210 |

(Continued)

FOREIGN PATENT DOCUMENTS

EP 0320895 6/1989

(Continued)

OTHER PUBLICATIONS

Denmark Office Action, dated Mar. 16, 2004, translation and Denmark application PA 2003 01549, filed Oct. 21, 2003.

(Continued)

*Primary Examiner*—Tatyana Zalukaeva
*Assistant Examiner*—Paula L Craig
(74) *Attorney, Agent, or Firm*—Marshall, Gerstein & Borun LLP

(57) ABSTRACT

An ostomy appliance having a face plate assembly and inner and outer pouches joined thereto, has its outer pouch provided with one or more peripherally-extending sealing seams that allow the walls of the outer pouch to be separated by peeling forces applied in directions transverse to such seam or seams. In preferred embodiments, the sealing seam, also peelably join the peripheral edges of the outer pouch to those of the inner pouch. A method of disposing of the pouch assembly of such an ostomy appliance is also disclosed.

35 Claims, 12 Drawing Sheets

U.S. PATENT DOCUMENTS

Figure 1:
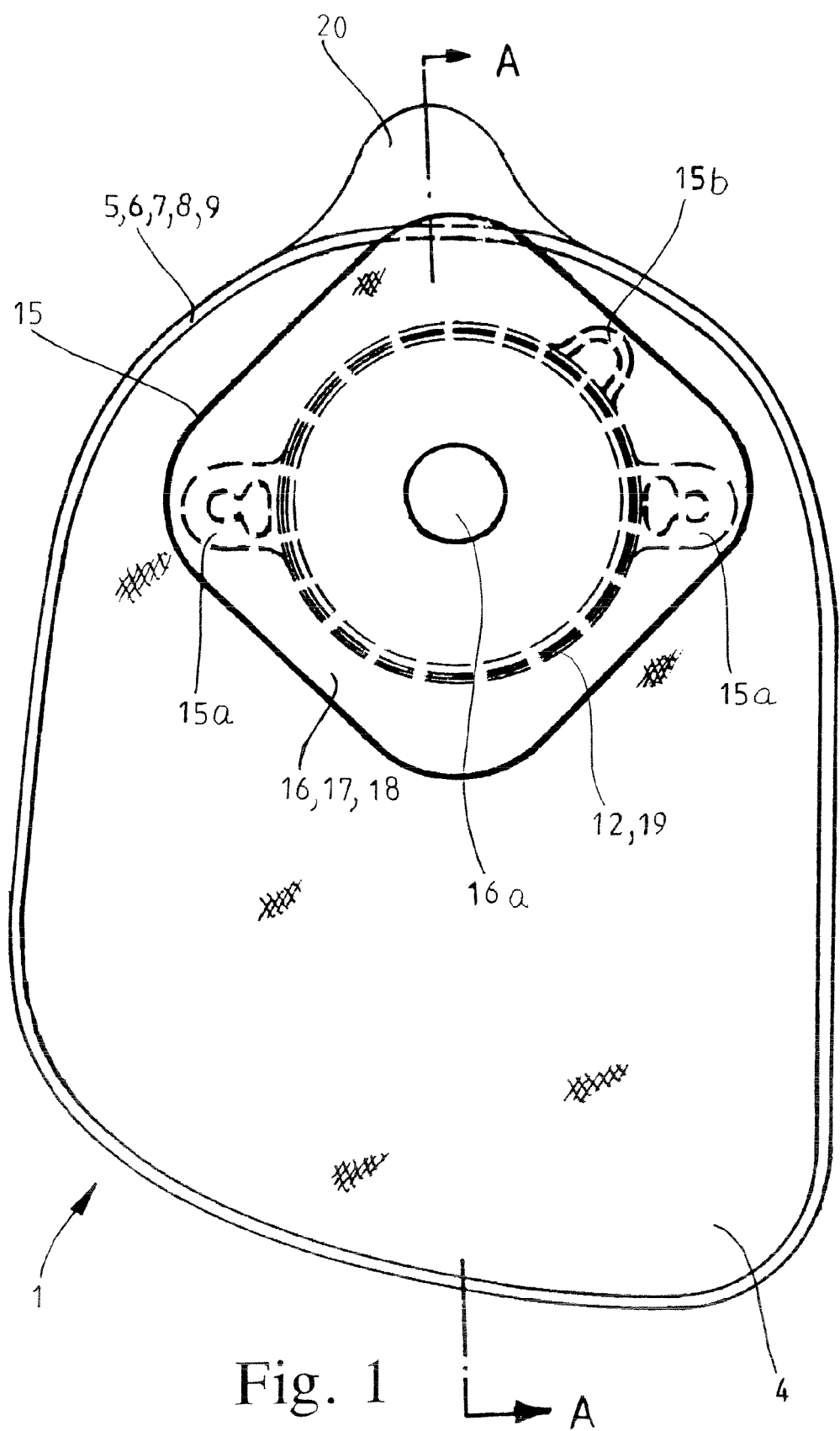

| | | | |
|---|---|---|---|
| 4,519,797 A | 5/1985 | Hall | |
| 4,687,711 A | 8/1987 | Vietto et al. | 428/515 |
| 4,705,512 A * | 11/1987 | Faucher | 604/332 |
| 4,762,738 A | 8/1988 | Keyes et al. | 428/34.3 |
| 4,772,279 A | 9/1988 | Brooks et al. | 604/339 |
| 4,816,027 A * | 3/1989 | Gilchrist et al. | 604/339 |
| 4,826,493 A | 5/1989 | Martini et al. | |
| 4,826,495 A | 5/1989 | Petersen | |
| 4,894,058 A * | 1/1990 | Jensen | 604/332 |
| 4,906,495 A | 3/1990 | Martini et al. | |
| 4,946,720 A | 8/1990 | Oishi et al. | |
| 5,009,648 A | 4/1991 | Aronoff et al. | |
| 5,026,362 A * | 6/1991 | Willett | 604/345 |
| 5,104,390 A | 4/1992 | Yum et al. | |
| 5,108,807 A | 4/1992 | Tucker | |
| 5,110,390 A | 5/1992 | Martini et al. | |
| 5,227,415 A | 7/1993 | Masuda et al. | |
| 5,250,042 A | 10/1993 | Torgalkar et al. | |
| 5,254,607 A | 10/1993 | McBride et al. | |
| 5,391,423 A | 2/1995 | Wnuk et al. | |
| 5,407,979 A | 4/1995 | Wu et al. | |
| 5,417,677 A | 5/1995 | Schneider et al. | |
| 5,422,387 A | 6/1995 | Toms et al. | |
| 5,423,782 A | 6/1995 | Wolrich | |
| 5,446,079 A | 8/1995 | Buchanan et al. | 524/41 |
| 5,455,091 A | 10/1995 | Oreglia et al. | |
| 5,468,526 A | 11/1995 | Allen et al. | |
| 5,470,526 A | 11/1995 | Wilfong et al. | 428/36.6 |
| 5,540,962 A | 7/1996 | Suskind | |
| 5,591,144 A | 1/1997 | Smith et al. | |
| 5,607,412 A * | 3/1997 | Brown | 604/332 |
| 5,651,777 A * | 7/1997 | Walters | 604/345 |
| 5,674,578 A * | 10/1997 | Giori | 428/35.4 |
| 5,679,421 A | 10/1997 | Brinton, Jr. | |
| 5,690,622 A * | 11/1997 | Smith et al. | 604/333 |
| 5,722,965 A * | 3/1998 | Kuczynski | 604/344 |
| 5,753,782 A | 5/1998 | Hammond et al. | 525/450 |
| 5,759,180 A * | 6/1998 | Myhres | 604/332 |
| 5,769,831 A | 6/1998 | Freeman et al. | |
| 5,776,120 A | 7/1998 | Shelley et al. | |
| 5,785,695 A | 7/1998 | Sato et al. | |
| 5,786,408 A | 7/1998 | Kuroda et al. | |
| 5,821,286 A | 10/1998 | Xu et al. | |
| 5,865,819 A | 2/1999 | Cisko, Jr. et al. | |
| 5,889,140 A | 3/1999 | Watanabe | 528/354 |
| 5,912,059 A * | 6/1999 | Jones et al. | 428/35.2 |
| 5,938,647 A | 8/1999 | Smith | |
| 5,939,467 A | 8/1999 | Wnuk et al. | |
| 5,969,089 A | 10/1999 | Narayan et al. | |
| 5,989,235 A * | 11/1999 | Quacquarella et al. | 604/332 |
| 6,033,758 A | 3/2000 | Kocher et al. | 428/138 |
| 6,075,118 A | 6/2000 | Wang et al. | |
| 6,110,156 A * | 8/2000 | Mendonca | 604/345 |
| 6,127,512 A | 10/2000 | Asrar et al. | |
| 6,156,929 A | 12/2000 | Chandler et al. | |
| 6,248,380 B1 | 6/2001 | Kocher et al. | 426/127 |
| 6,248,442 B1 | 6/2001 | Kong et al. | 428/355 EN |
| 6,468,254 B2 * | 10/2002 | Gupton | 604/345 |
| 6,514,602 B1 | 2/2003 | Zhao et al. | |
| 6,552,162 B1 | 4/2003 | Wang et al. | 528/354 |
| 7,045,183 B2 | 5/2006 | Amano et al. | 428/35.2 |
| 7,179,245 B2 * | 2/2007 | Giori | 604/332 |
| 7,214,217 B2 * | 5/2007 | Pedersen et al. | 604/333 |
| 2002/0016578 A1 * | 2/2002 | Gupton | 604/345 |
| 2002/0064614 A1 | 5/2002 | Turnbull | |
| 2002/0197425 A1 | 12/2002 | Wolf et al. | 428/35.2 |
| 2003/0204174 A1 * | 10/2003 | Cisko, Jr. | 604/338 |
| 2004/0059306 A1 * | 3/2004 | Tsal et al. | 604/332 |
| 2007/0203466 A1 * | 8/2007 | Pedersen et al. | 604/333 |
| 2007/0261789 A1 * | 11/2007 | Giori | 156/308.4 |

FOREIGN PATENT DOCUMENTS

| | | |
|---|---|---|
| EP | 0611123 | 8/1994 |
| EP | 0 703 762 B1 | 2/1998 |
| EP | 0703762 B1 | 2/1998 |
| EP | 0 833 596 B1 | 4/1998 |
| EP | 1 022 127 A2 | 7/2000 |
| EP | 0443728 B9 | 8/2002 |
| GB | 2 083 762 A | 3/1982 |
| GB | 2 227 668 | 8/1990 |
| WO | WO 94/28061 | 12/1994 |
| WO | WO-01/10363 | 8/2000 |
| WO | WO-01/82846 | 11/2001 |

OTHER PUBLICATIONS

International Search Report and Written Opinion from PCT/US04/34759.

International Search Report from PCT/US2004/034760, mailed Sep. 1, 2005.

Written Opinion of the International Searching Authority from PCT/US2004/034760, mailed Sep. 1, 2005.

* cited by examiner

PEELABLE AND FLUSHABLE OSTOMY POUCH AND METHOD OF USE

RELATED APPLICATIONS

This application claims priority from U.S. Provisional Patent Application Ser. No. 60/512,760 filed Oct. 21, 2003 and Danish Patent Application Ser. No. 2003/01549, filed Oct. 21, 2003.

BACKGROUND AND SUMMARY

The present invention relates to an ostomy appliance for receiving discharge from a human stoma and comprising:

attachment means for attaching the appliance to the peristomal skin surface of a user of the appliance, and
an ostomy pouch assembly comprising:
an inner pouch attached to said attachment means and having a first aperture for receiving the stoma of said user,
said inner pouch being defined by a flexible body side or proximal inner pouch wall and a flexible distal inner pouch wall, and one or more peripherally extending inner pouch sealing seams,
an outer pouch enclosing said inner pouch, attached to said attachment means and having a second aperture for receiving said stoma and being aligned with said first aperture,
said outer pouch being defined by a flexible body side or proximal outer pouch wall and a flexible distal outer pouch wall, and one or more peripherally extending outer pouch sealing seams.

In connection with the disposal of the pouch assembly or the entire ostomy appliance after use thereof when the inner pouch is more or less full of stomal discharge, it is important that this can be done in a manner that is convenient for the user of the appliance. This entails that it should not be necessary to carry the full inner pouch to a disposal site outside the premises in which the full pouch is to be exchanged with a new, empty pouch. The best solution to this disposal problem is to flush the inner pouch out through a toilet.

Many solutions to this problem have been suggested, for instance in EP 0 703 762, EP 0 611 123, U.S. Pat. No. 4,372,308, GB 2227668, WO 0182846, EP 0 703 762, U.S. Pat. Nos. 5,938,647, 5,769,831 and 5,455,091, the disclosure of which is hereby incorporated herein by reference.

A fully satisfactory solution has not yet been obtained where the inner pouch can easily flow through the sewage system and not cause clogging and overloading of the sewage treatment facilities, where the separation of the inner pouch from the rest of the appliance can be achieved in an easy and secure manner and where the rest of the pouch assembly can be disposed of in a convenient and hygienic manner.

It is a main object of the invention to provide an ostomy appliance where the above listed requirements have been met to a higher degree than before.

According to the invention, this object is achieved by said one or more outer pouch sealing seams being manually peelable such that the attachment forces provided by said one or more peelable outer pouch sealing seams may be manually eliminated by manually pulling said outer pouch wall in a direction transverse to said one or more peelable outer pouch sealing seams.

Hereby, separation forces are applied to said one or more peelable outer pouch sealing seams in a direction transverse thereto so as to peel said outer pouch wall away from the rest of the pouch assembly whereby the inner pouch can be exposed in a simple and convenient manner that does not require any special dexterity.

In the currently preferred embodiment of an ostomy appliance according to the invention, said one or more outer pouch sealing seams peelably attach said distal outer pouch wall to said distal inner pouch wall and said proximal outer pouch wall to said proximal inner pouch wall.

Hereby a particularly simple embodiment is achieved, where the inner pouch sealing seam and the outer pouch sealing seams may be carried out in one single sealing operation.

Alternatively, said one or more outer pouch sealing seams may peelably attach said distal outer pouch wall directly to said proximal outer pouch wall.

Furthermore said one or more outer pouch sealing seams may peelably attach said distal outer pouch wall partly to said proximal outer pouch wall and partly to said distal inner pouch wall and peelably attach said proximal outer pouch wall to said distal outer pouch wall and partly to said proximal inner pouch wall.

In said currently preferred embodiment, the inner pouch is attached to said attachment means by a peelable interior sealing seam extending around said stoma receiving aperture in said inner pouch. Hereby, the inner pouch can be detached from the attachment means in a simple and convenient manner that does not require any special dexterity.

In said currently preferred embodiment, the material of said inner pouch walls is biodegradable. Hereby, the load on the sewage treatment plants is reduced.

In said currently preferred embodiment said inner pouch walls are made of a plastic film laminated to a web of a non-woven fibrous material such as paper, preferably a paper of a toilet tissue type, said web facing outwards relative to the interior of said inner pouch.

Hereby, a particularly efficient and simple manner of obtaining a peelable sealing seam between the inner pouch walls and the outer pouch walls is obtained, and tissue paper readily disintegrates in water so that when discarded into a flush toilet, the fibres of the paper, which are preferably cellulosic and biodegradable, although not soluble in water, quickly disperse.

Furthermore, the use of paper as the outer layer of the inner pouch laminated walls affords important advantages regarding the dry strength of the inner pouch, the soft feel and appearance of the inner pouch and the disposability of the inner pouch by being flushed through a toilet.

Paper in dry condition has a relatively large tensile strength, and thus laminating paper on to a film of plastic material allows using a thinner film for achieving liquid and gas impermeability as well as sufficient combined strength. This is advantageous from an economic viewpoint, as less relatively expensive plastic material is required for the inner pouch walls. However, the main advantage is that the relatively thin film when deprived of the dry strength of the paper after being submerged in water is prone to being broken up into more easily degraded fragments such that the effect on the sewage treatment systems is greatly reduced.

In said currently preferred embodiment, said non-woven material and/or said plastic film are biodegradable.

In said currently preferred embodiment, said inner pouch walls are impermeable to liquid and gas and permeable to odours, and said outer pouch walls are impermeable to liquid, gas and odours. This allows the use of a very thin liquid and gas barrier for the inner pouch walls which is of particular importance for the environmental impact thereof.

Preferably, said one or more outer pouch peeling seams comprises a peeling action initiation zone, where said one or more outer pouch sealing seams comprises a peak-like extent tapering in the direction opposite a predetermined peeling direction. Hereby, the area of the peeling seam where the peeling action is to be initiated is reduced thereby facilitating the peeling operation.

Preferably, said one or more outer pouch peeling seems comprises a peeling action ending zone, where said one or more outer pouch sealing seams comprises a peak-like extent tapering in a predetermined peeling direction. Hereby, the area of the peeling seam where the peeling action is to be ended is reduced thereby facilitating the peeling operation.

Preferably, said interior inner pouch sealing seam comprises a peeling action initiation zone, where interior inner pouch sealing seam comprises a peak-like extent tapering in the direction opposite a predetermined peeling direction, and said interior inner pouch sealing seam comprises a peeling action ending zone, where interior inner pouch sealing seam comprises a peak-like extent tapering in a predetermined peeling direction.

In said currently preferred embodiment, said proximal outer pouch wall is attached to said attachment means by a heat sealed sealing seam. Hereby at least part of the attachment means can be disposed of together with the outer pouch walls.

Alternatively, said proximal outer pouch wall is attached to said attachment means by a peelable sealing seam. Hereby, the attachment means may be disposed of separate from the outer pouch walls.

In one embodiment of a so-called two-piece ostomy appliance according to the invention, said attachment means comprise a face plate assembly comprising a wafer of skin friendly adhesive material having a third aperture for receiving said stoma aligned with said first and second apertures, and a first coupling ring surrounding said third aperture and attached to said wafer and in engagement with a second coupling ring surrounding said first and second apertures and attached to said proximal outer pouch wall and to said proximal inner pouch wall.

In a currently preferred embodiment of a two-piece ostomy appliance according to the invention, said proximal outer pouch wall is attached to said second coupling ring by means of a heat sealed sealing seam. Hereby, the second coupling ring is fixedly attached to the outer pouch wall for disposal therewith.

Advantageously, said proximal inner pouch wall is attached to said second coupling ring by means of said peelable interior sealing seam. Hereby, the inner pouch may be disposed of separately from the second coupling ring.

In said currently preferred embodiment, said proximal inner pouch wall is attached to said proximal outer pouch wall in a region surrounding said first and second apertures by means of said peelable interior sealing seam. Hereby, the inner pouch may be manually separated from the outer pouch in a simple and convenient manner.

In a second embodiment of a two-piece ostomy appliance according to the invention, said attachment means comprise a face plate assembly comprising a wafer of skin friendly adhesive material having a third aperture for receiving said stoma aligned with said first and second apertures, and a first coupling means surrounding said third aperture and attached to said wafer and in releasably adhesive engagement with a second coupling means surrounding said first and second apertures and attached to said proximal outer pouch wall and/or to said proximal inner pouch wall.

The proximal outer pouch wall may attached to said second coupling means by means of a heat sealed sealing seam, and said proximal inner pouch wall may be attached to said second coupling means by means of said peelable interior sealing seam, or said proximal inner pouch wall may be attached to said proximal outer pouch wall in a region surrounding said first and second apertures by means of said peelable interior sealing seam.

In a so-called one-piece ostomy appliance according to the invention, said attachment means comprise a face plate assembly comprising a wafer of skin friendly adhesive material having a fourth aperture for receiving said stoma aligned with said first and second apertures, and a carrier sheet attached to the distal surface of said wafer and attached to said proximal outer pouch wall and to said proximal inner pouch wall.

In a currently preferred embodiment, of a one-piece ostomy appliance according to the invention, said proximal outer pouch wall is attached to said carrier sheet by means of a heat sealed sealing seam.

Advantageously, said proximal inner pouch wall is attached to said carrier sheet by means of said interior peelable sealing seam.

In said currently preferred embodiment, said proximal inner pouch wall is attached to said proximal outer pouch wall in a region surrounding said first and second apertures by means of said peelable interior sealing seam.

In said currently preferred embodiment, said peelable interior sealing seam is constituted by a sheet of film or textile with a fifth stoma receiving aperture and having adhesive on both opposed surfaces. This affords a particularly secure peelable adhesion between the inner pouch and the rest of the appliance.

Advantageously, an annular insert having a sixth aperture for receiving said stoma is provided within said second coupling ring for preventing said stomal discharge from soiling said second coupling ring. Hereby, the second coupling ring can be disposed of in a hygienic manner because it is not soiled by the stomal discharge.

The attachment forces provided by said one or more peelable outer pouch sealing seams are preferably such that the pulling force required for manually eliminating said attachment forces is between approx. 0.5 Newton and approx. 6 Newton, preferably between approx. 0.7 Newton and approx. 5.5 Newton, even more preferably between approx. 0.8 Newton and approx. 5.0 Newton, even more preferably between approx. 0.9 Newton and approx. 4.5 Newton and most preferably between approx. 1.0 Newton and approx. 4.0 Newton.

Hereby the pulling or peeling force is such that the risk of unintended ripping of the outer pouch walls and especially the inner pouch walls is minimal during peeling of the outer pouch sealing seams while the attachment forces are sufficient to ensure the integrity of the pouch assembly during use thereof.

In said currently preferred embodiment, said outer pouch peelable sealing seams are between 4 and 6 mm wide, preferably approximately 5 mm wide. It has turned out that this affords the best balancing of easy peelability and secure fastening of the pouch walls to one another during use of the pouch assembly.

In said currently preferred embodiment, at least a portion the outer peripheral edges of said outer pouch walls and inner pouch walls has been formed by cutting through said walls in the areas of said outer pouch peelable seams. The cutting friction creates a melting zone at the edge of the outer and inner pouches that prevents wicking of water from a shower or bath into the peelable sealing seams containing a fibrous material between the inner pouch walls and the outer pouch walls.

In said currently preferred embodiment, a portion of said outer pouch walls and inner pouch walls extend beyond said outer pouch peelable seams to form inner pouch wall and outer pouch wall gripping tabs for peeling said walls apart. Hereby, a particularly simple and easily implemented peeling function is obtained.

In said currently preferred embodiment, said outer pouch peelable seams are made by applying heat and/or RF to the outer surface of one or both of said outer pouch walls.

In said currently preferred embodiment, an area of each of said inner pouch wall gripping tabs extending into the area covered by the adjacent outer pouch peelable seam has been subjected to application of heat and/or RF prior to the formation of said outer pouch peelable seams. Hereby wicking of water from a shower or a bath is prevented in the region of the tabs into the peelable seams containing a fibrous material between the inner pouch walls and the outer pouch walls.

In said currently preferred embodiment, the fibres of said paper have a generally uniform orientation and said orientation is transversal to a line extending from the top to the bottom of said outer and inner pouches when a user to which said pouches have been applied around a stoma is standing erect, said orientation preferably being generally orthogonal to said line. Hereby, a particularly neat and uniform peeling is obtained where most of the paper remains attached to the inner pouch walls after peeling.

In another aspect, the present invention relates to an ostomy pouch assembly for use in an ostomy appliance according to the invention.

In a further aspect, the present invention relates to an inner pouch for use in an ostomy appliance according to the invention.

In a yet further aspect, the present invention relates to a method of disposing of an ostomy pouch assembly of an ostomy appliance as specified above after use thereof, said method comprising the steps of:

gripping an edge portion of said distal outer pouch wall, pulling said edge portion of said distal pouch wall away from the body of the user such that the attachment of said distal outer pouch wall by the respective one of said one or more peelable outer pouch sealing seams to the rest of said appliance is disrupted, gripping mutually superimposed edge portions of said distal and proximal inner pouch wall, pulling said superimposed edge portions away from the body of the user such that the attachment of said inner pouch by the respective peelable sealing seams to the rest of said appliance is eliminated, and disposing of the inner pouch with contents in a toilet bowl.

In a final aspect, the present invention relates to the use of a flexible composite film made of a plastic film laminated to a web of a non-woven fibrous material such as paper, preferably a paper of a toilet tissue type, for providing a peelable sealing seam between an inner pouch and an outer pouch of an ostomy appliance, said inner pouch being surrounded and enclosed by said outer pouch, and the walls of said inner pouch being made of said composite film with said web facing outwards relative to the interior of said inner film.

In the following, the invention will be explained more in detail with reference to various embodiments of the invention shown, solely by way of example, in the drawings.

DRAWINGS

Figure 2:
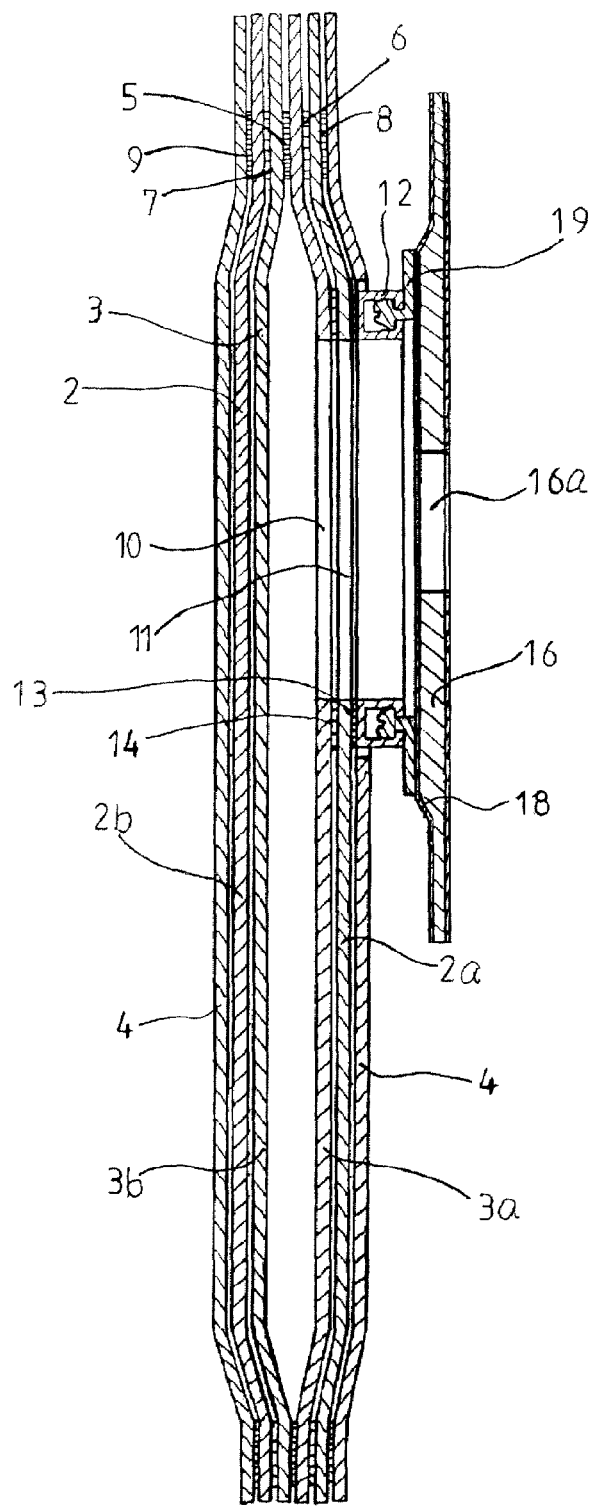
Figure 3:
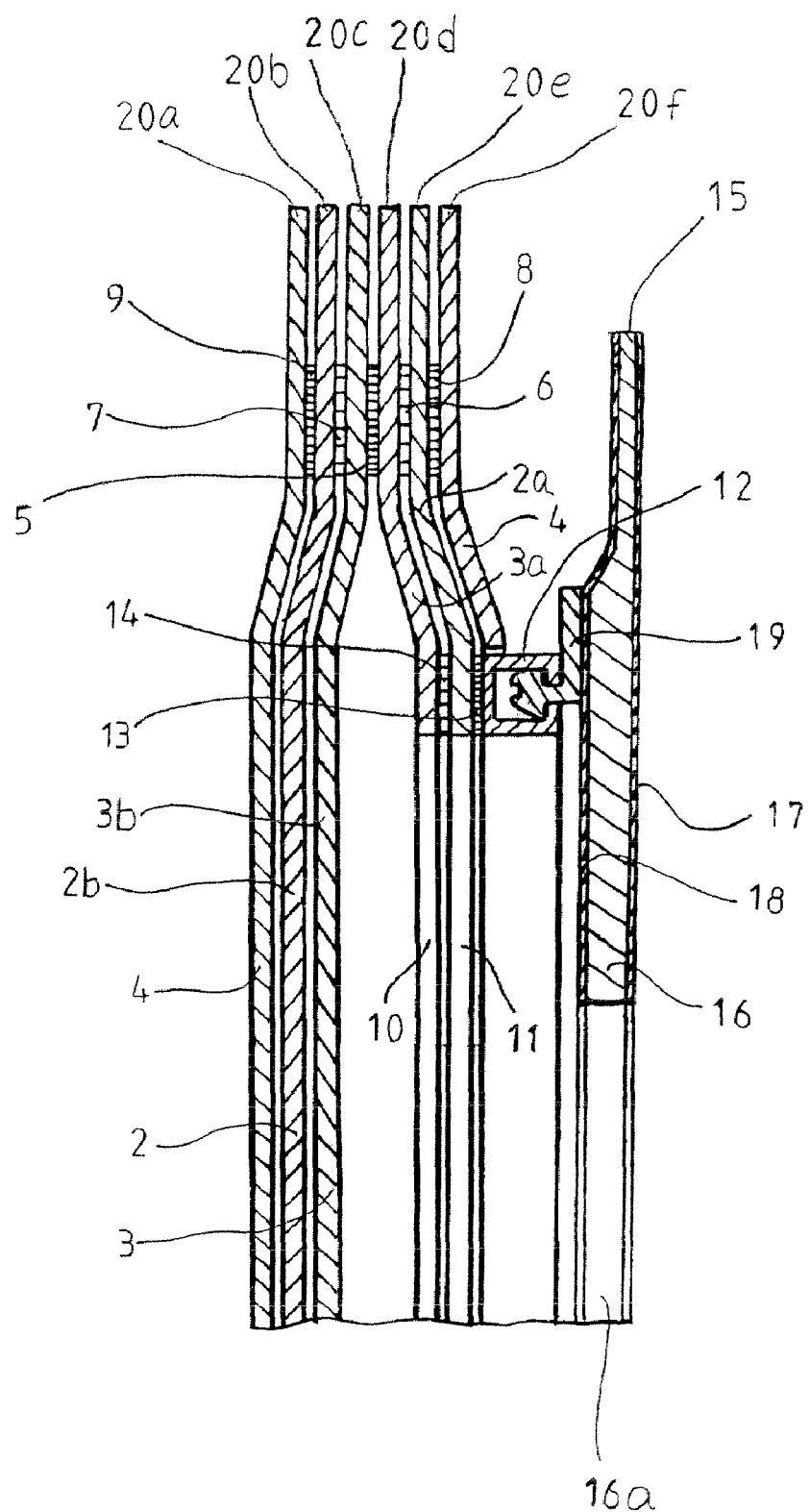
Figure 4:
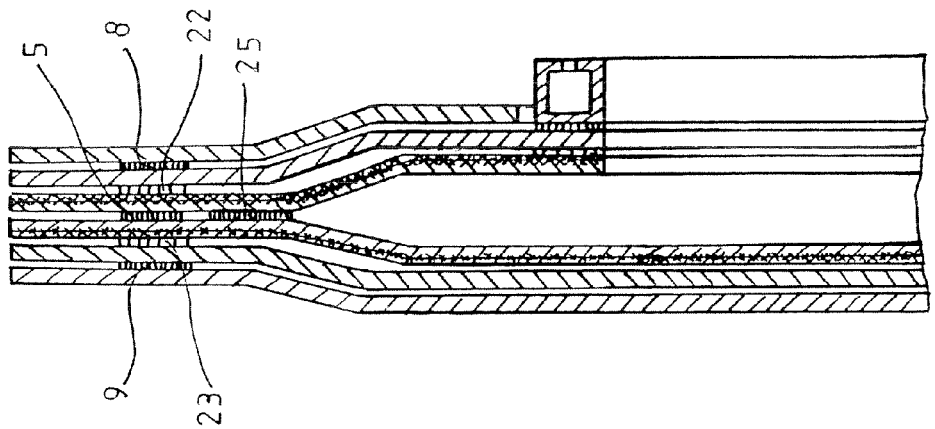
Figure 5:
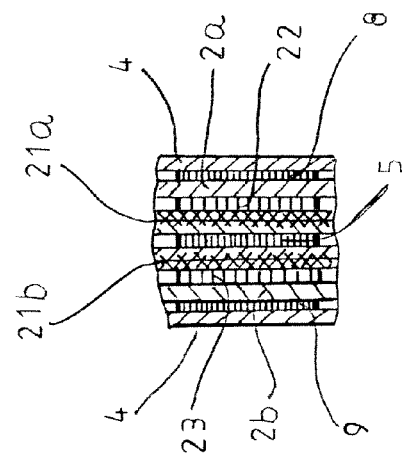
Figure 6:
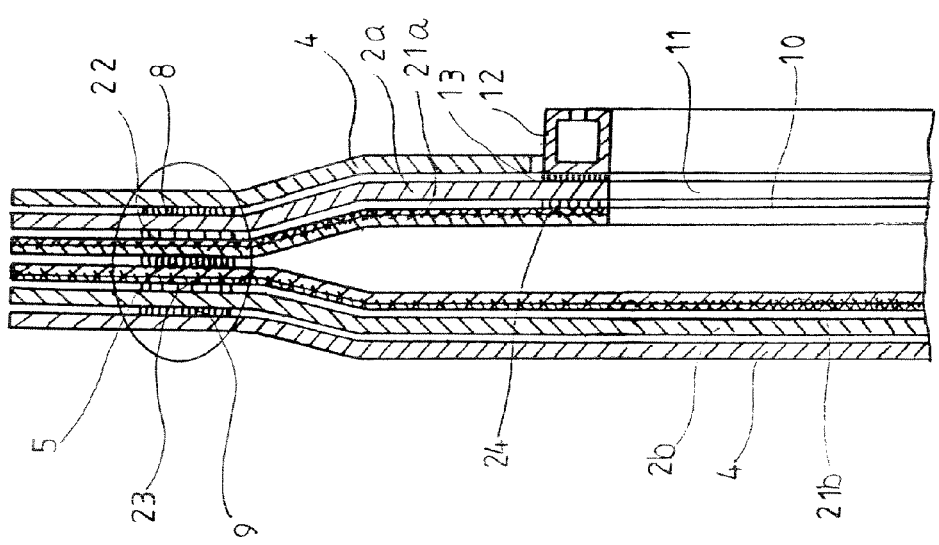
Figure 7:
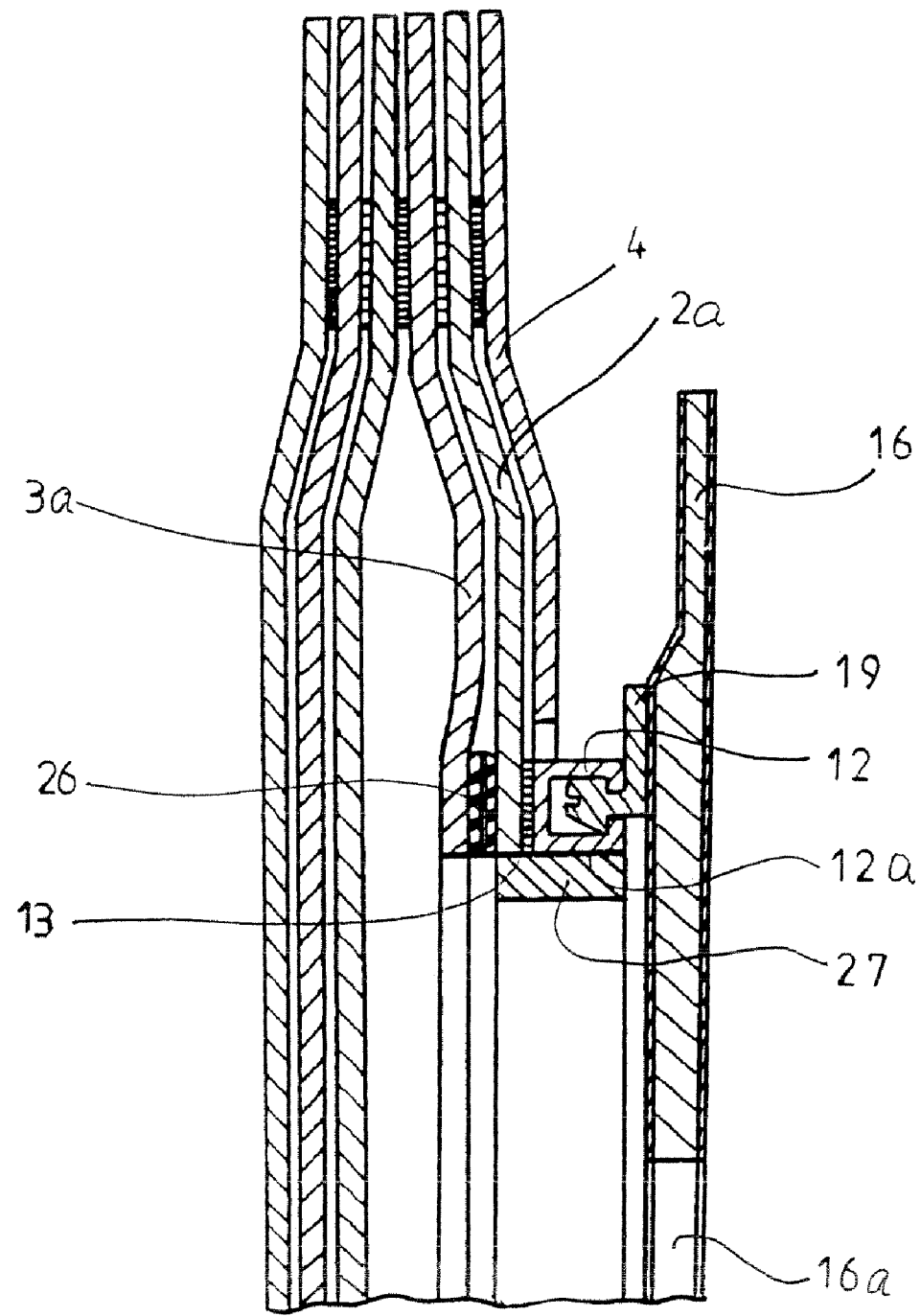
Figure 9:
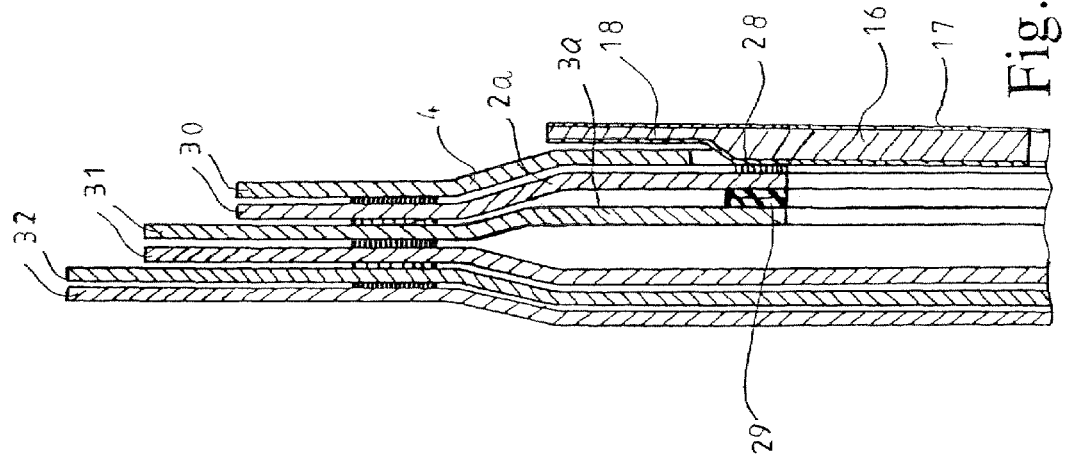
Figure 8:
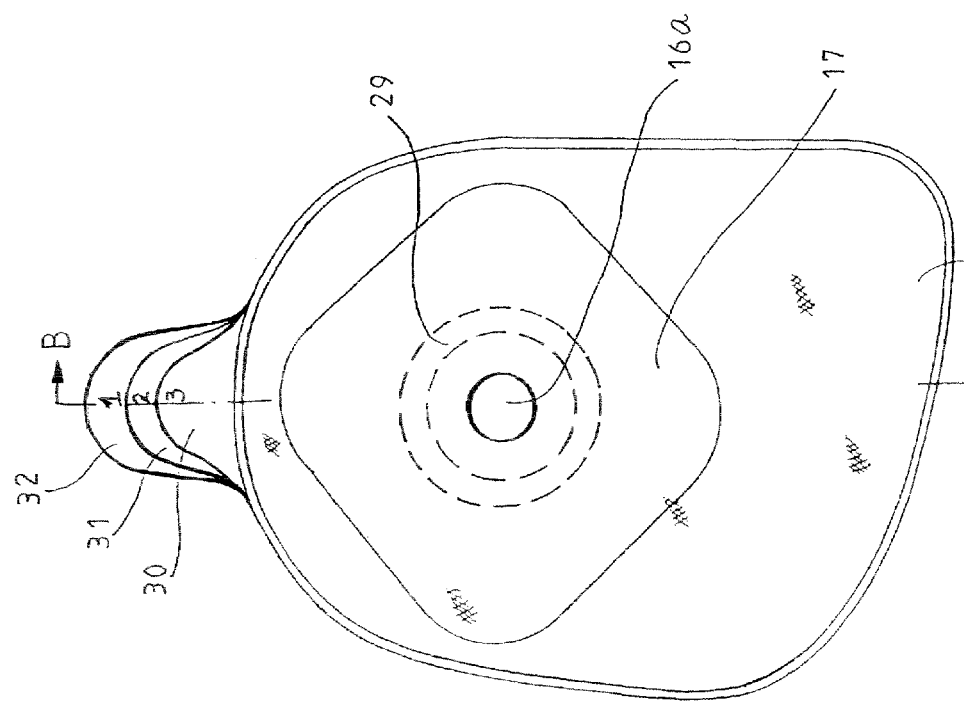
Figure 10:
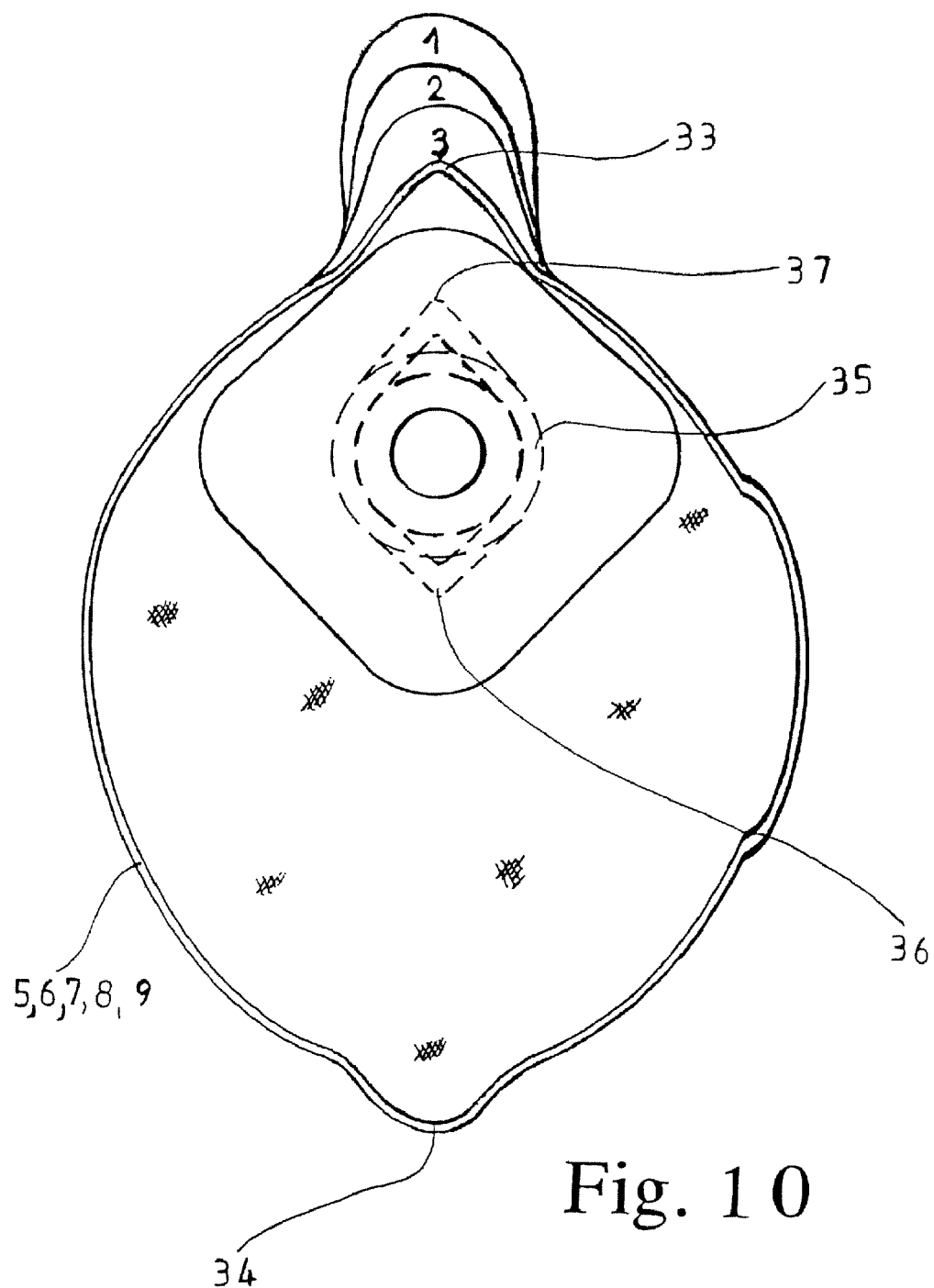

FIG. 1 is a schematic plan view, seen from the body side, of a first embodiment of a two-piece ostomy pouch according to the invention, FIG. 2 is a diagrammatic cross sectional view taken along line A-A in FIG. 1 with the film thicknesses exaggerated for illustrative purposes, FIG. 3 is an enlarged scale view of the top portion of FIG. 2, FIG. 4 is a cross sectional view corresponding to FIG. 3 of a second embodiment of the ostomy appliance according to the invention, FIG. 5 is an enlarged scale view of the area encircled in FIG. 4, FIG. 6 is a view corresponding to FIG. 4 of a modification of the embodiment of FIGS. 4-5, FIG. 7 is a view corresponding to FIG. 4 of a further embodiment of a two-piece ostomy appliance according to the invention, FIG. 8 is a schematic plan view, seen from the body side, of a first embodiment of a one-piece ostomy pouch according to the invention, FIG. 9 is a diagrammatic broken away, cross sectional view of the top portion of the appliance of FIG. 8 taken along line B-B in FIG. 8 with the film thicknesses exaggerated for illustrative purposes, FIG. 10 is a view corresponding to FIG. 8 of a second embodiment of a one-piece ostomy pouch according to the invention.

Figure 11:
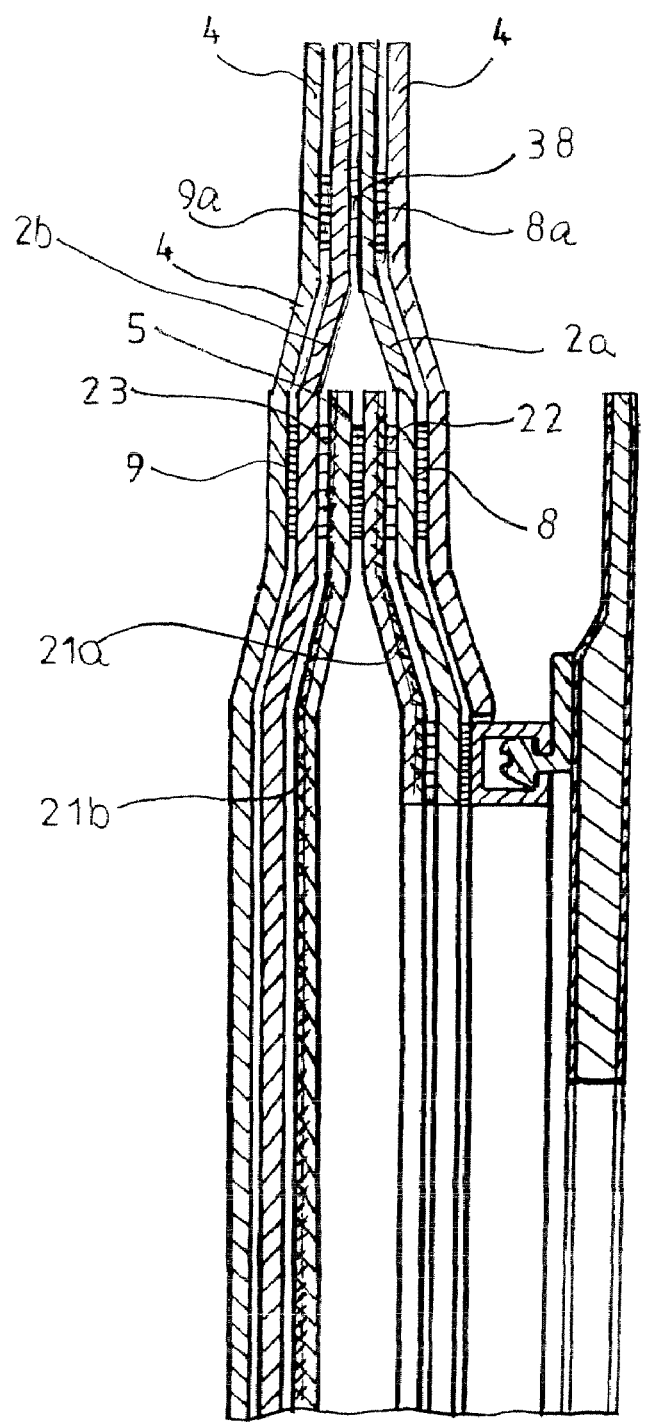
Figure 12:
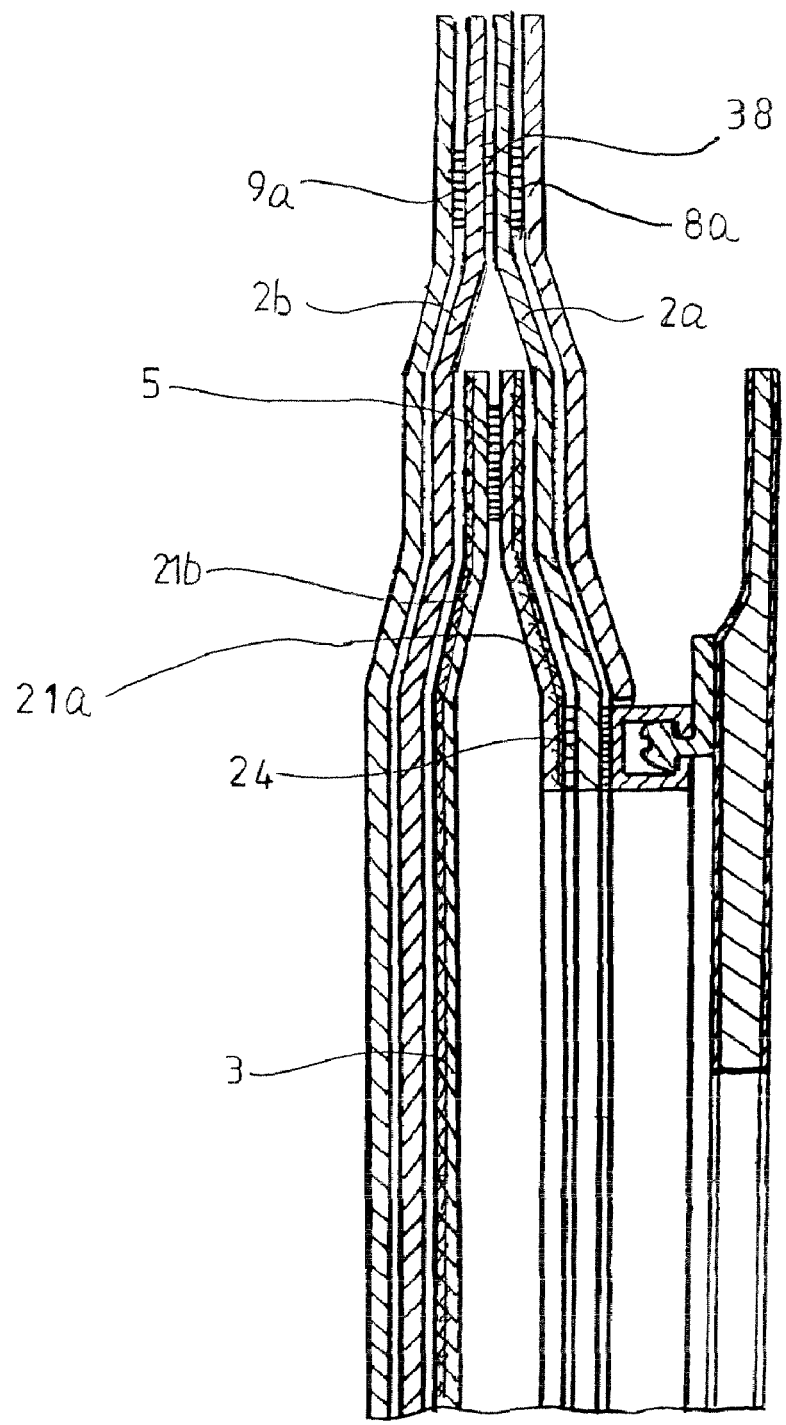
Figure 13:
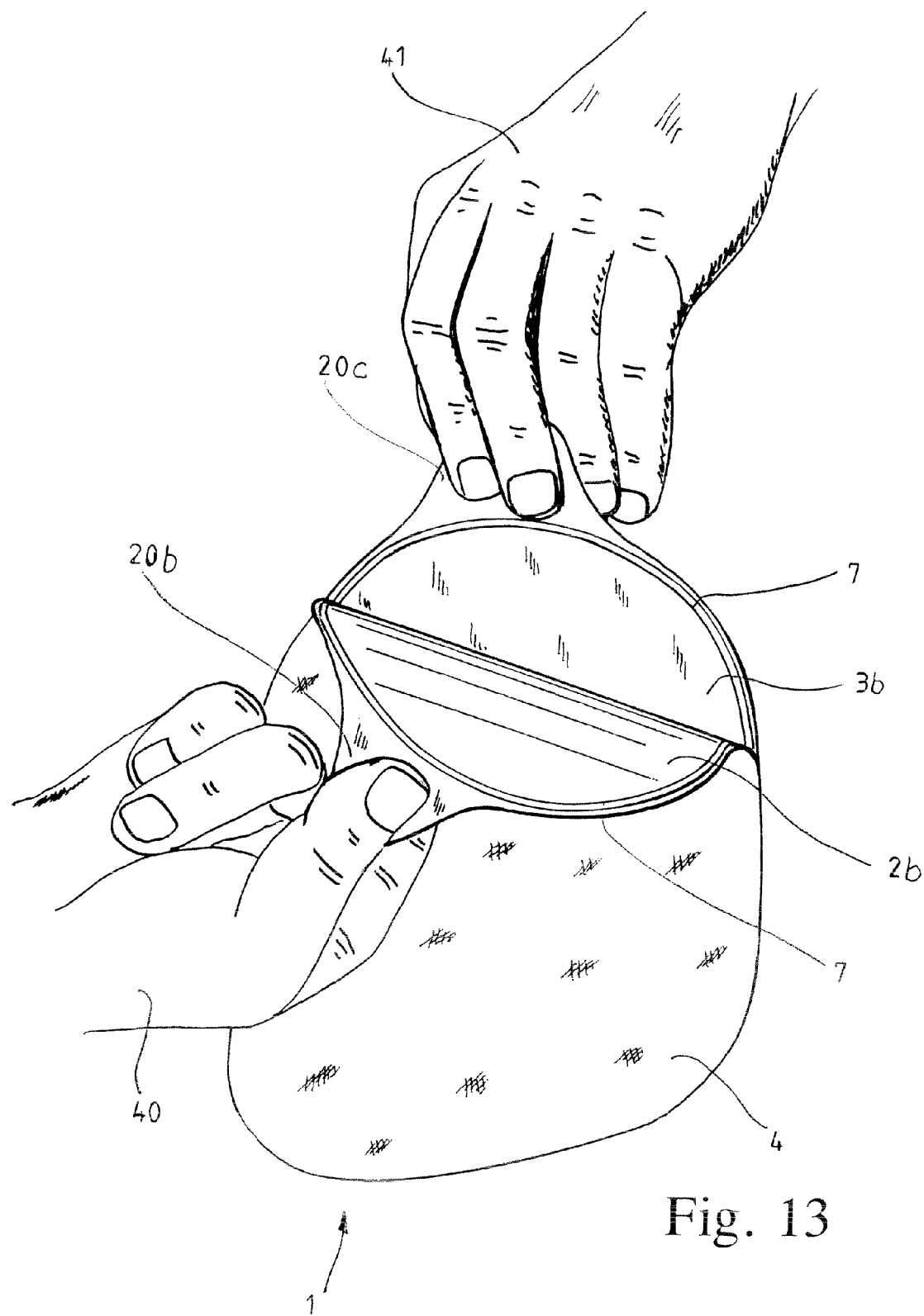
Figure 14:
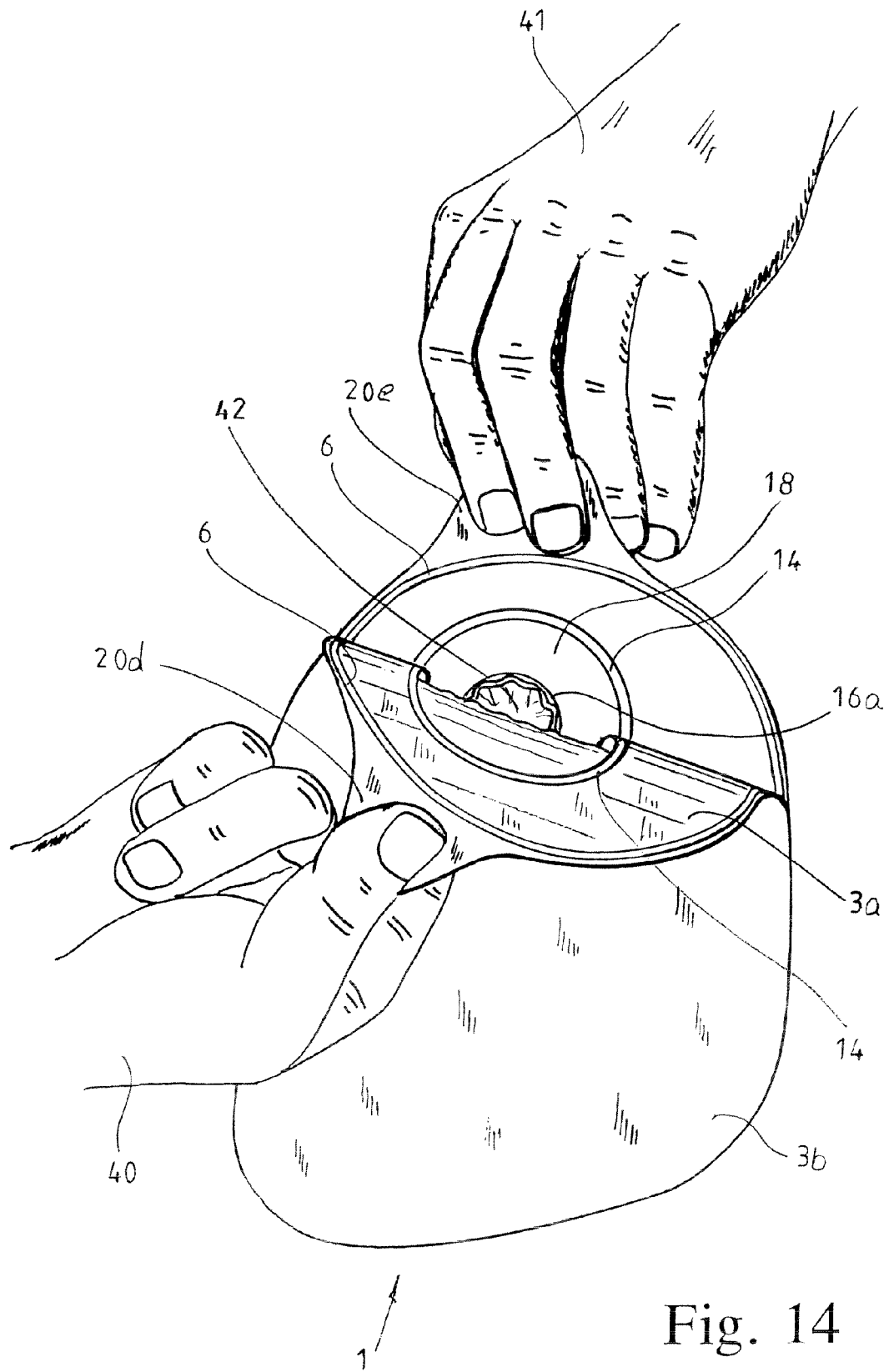
Figure 15:
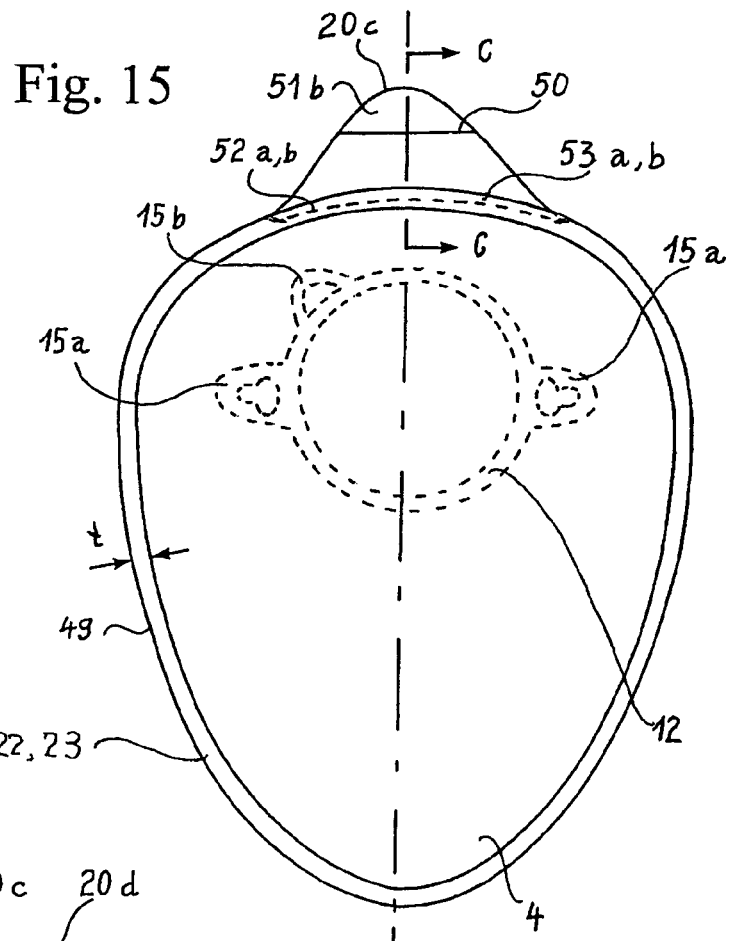
Figure 16:
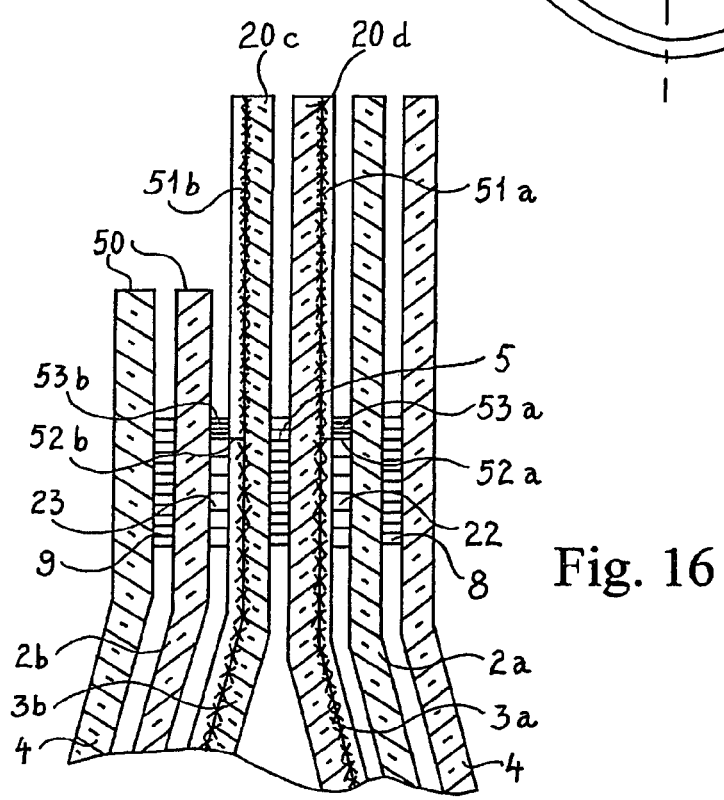

FIG. 11 is a view corresponding to FIG. 4 of a further embodiment of a two-piece ostomy appliance according to the invention, FIG. 12 is a view corresponding to FIG. 4 of a yet further embodiment of a two-piece ostomy appliance according to the invention, FIG. 13 is a schematic frontal view seen in the direction towards the body of the user of an ostomy appliance according to the invention illustrating the peeling off of the distal outer pouch wall, FIG. 14 is a view similar to FIG. 13 illustrating the peeling off of the inner pouch, FIG. 15 is a schematic plan view, seen from the distal side, of the currently preferred embodiment of a two-piece ostomy pouch according to the invention, and FIG. 16 is a diagrammatic cross sectional enlarged scale view taken along line C-C in FIG. 15 with the film thicknesses exaggerated for illustrative purposes.

DETAILED DESCRIPTION OF PREFERRED EMBODIMENTS

Referring now to FIGS. 1-3, an ostomy appliance referenced generally by the numeral 1 comprises an outer pouch 2 comprised of a body side or proximal wall 2a and an opposed distal wall 2b. The appliance furthermore comprises an inner pouch 3 comprised of a proximal wall 3a and a distal wall 3b. The outer pouch walls 2a and 2b are covered by a comfort layer 4 of +a non-woven material.

The walls 2a and 2b are made of a flexible plastic film that is impermeable to liquids, gasses and odours. The walls 3a and 3b are made of a flexible plastic film that is impermeable to liquids and gasses and permeable to odours.

The inner pouch 3 is formed by sealingly securing the two inner walls 3a and 3b to each other along the peripheries thereof by means of an inner pouch seam 5 either being a heat sealing seam or an adhesive seam.

The outer pouch 2 is formed by sealing the proximal and distal outer pouch walls 2a and 2b, respectively, to the inner pouch proximal and distal walls 3a and 3b, respectively by means of peelable sealing seams 6 and 7, respectively, extending along the outer periphery of the outer and inner pouch walls.

The comfort layers 4, which are optional, are sealed to the outer pouch walls 2a and 2b by means of heat sealing or adhesive seams 8 and 9, respectively, extending along the outer periphery of the outer pouch walls.

Both the inner pouch 3 and the outer pouch 2 have a stoma receiving aperture 10 and 11, respectively in the proximal walls 3a and 2a, respectively.

The appliance 1 further comprises a pouch coupling ring 12 secured to the proximal outer pouch wall 2a by means of a circumferential heat seal 13 or other suitable means. The area surrounding the aperture 10 of the proximal inner pouch wall 3a is attached to the corresponding area of the proximal outer pouch wall 2a by means of an annular peelable seam 14.

The appliance 1 further comprises a face plate assembly 15 having an adhesive layer 16 for adhering the face plate assembly to the peristomal surface of a user of the appliance 1 after having removed a release sheet 17 covering the proximal or body side surface of the adhesive layer 16. The adhesive layer is provided with a stoma receiving aperture 16a.

A carrier sheet 18 is attached to the distal surface of the adhesive layer 16, and a face plate coupling ring 19 is secured to the carrier sheet 18, such that interconnection of the two coupling rings 12 and 19 as shown in FIG. 2 will allow the pouch assembly 2, 3 to be adhered to the peristomal skin surface of a user with the stoma inserted in the apertures 16a, 10 and 11 such that stomal discharge may enter the inner pouch 3. The face plate coupling ring 19 is provided with two optional belt loops 15a and an optional burp tab 15b.

The inner and outer walls 2a, 2b, 3a, 3b as well as the comfort layers 4 project outwardly and upwardly are prolonged at the top of the appliance to form a tongue or projection 20 for providing non-connected and separable gripping tabs 20a-20f for the separation of the two pouches for disposal thereof as explained below in connection with FIGS. 13 and 14.

In use, when the inner pouch is full of stomal discharge and the pouch needs to be replaced by an empty pouch, the user or a helper (see FIGS. 3 and 13) grips the tabs 20a and 20b together with one hand 40 and the rest of the tabs with the other hand 41 and pulls the tabs 20a and 20b away from the body and downwardly. Hereby the connection between the outer pouch wall 2b and the inner pouch wall 3b by means of the peelable sealing seam 7 is broken or disrupted such that the proximal outer pouch wall 2b with its comfort layer 4 is peeled away from the appliance 1.

Thereafter, the user (see FIGS. 3 and 14) grips the tabs 20c and 20d together with one hand 40 and the tabs 20e and 20f with the other hand 41 and pulls the tabs 20c and 20d outwardly and downwardly whereby the peelable sealing seam 6 gives way so that the inner pouch 3 is peeled away from the outer pouch proximal wall 2a until the level of the top point of the peelable sealing seam 14 is reached. This peelable seam 14 also gives way to the pulling force exerted on the tabs 20c and 20d so that finally the entire inner pouch 3 with its content of stomal discharge has been peeled away from the proximal outer pouch wall 2a. The stoma 42 of the user is now exposed (see FIG. 14).

Now the inner pouch 3 with contents can be deposited in the bowl of a toilet and flushed away while the proximal outer pouch wall 2a with comfort layer 4 and coupling ring 13 can be removed from the face plate assembly 15. The outer pouch walls 2a and 2b with corresponding comfort layers 4 and the coupling ring can now be folded together and be disposed of in some other manner, for instance in a pocket, a hand bag or a refuse container.

The material of the inner and outer pouch walls may be a film of any suitable plastic material. The outer pouch wall film material is impermeable to liquids, gasses, while the inner pouch wall film is impermeable to liquids and gasses, but not necessarily to odours. By allowing the inner pouch wall film to be permeable to odours, the film may be made thinner and thus be more easily disintegrated and biodegraded.

It is preferable that the inner pouch wall film material be biodegradable so that the sewage treatment facilities are not inconvenienced to an unnecessary degree. By allowing the inner pouch wall film to be permeable to odours, the film may be made thinner and thus be more easily disintegrated and biodegraded.

Examples of biodegradable films suitable for the inner pouch walls 3a and 3b are biodegradable aliphatic polyesters such as polycaptrolactone.

A biodegradable and liquid impermeable material that currently is considered suitable for the inner pouch wall film are biodegradable aliphatic polyesters such as polycaprolactone (for instance TONE Polymer supplied by Dow Chemical Company) or a biodegradable aliphatic-aromatic copolyester (for instance ECOFLEX supplied by BASF).

The peelable sealing seams 6, 7 and 14 may be provided in various ways, for instance by utilizing a peel lacquer or varnish which gives a peelable adhesion to either the inner or the outer pouch walls or to both walls. The type of peelable lacquer or varnish depends on the material chosen for the pouch bag films.

Peel lacquers that currently are considered to be suitable for certain film materials are "Appeel" resins from the company duPont, and hot melt peelable adhesives supplied under the trade names Dispomelt 34-2881, 34-5519, Instaweld 34-3306 and Bondmaster 34-3306 by the companies National Starch Adhesive and Chemical Corporation.

Another way of implementing the peelable sealing seams is to use an intermediate film of polybutylene or an intermediate three-layer film supplied by the company Rexam under the trade name Core-Seal, the peeling occurring between the two outer films and the internal film or layer, the external films being securely heat sealed to the inner and outer pouch wall films.

A further way of implementing the peelable seams is to use a silicone release film such as the type used for labels.

In the context of the present invention, the term peelable utilised in the specification and claims is to be understood to mean that the connection between two films, be it by means of an adhesive, heat sealing or other means, can be broken, disrupted or eliminated by manually urging one film away from the other without compromising the integrity of the films.

A currently preferred manner of providing peelable sealing seams will now be described with reference to FIGS. 4-5. The embodiment of FIGS. 4-5 is identical to the embodiment of FIGS. 1-3 except for the inner pouch bag walls 21a and 21b that are made of a heat sealable, liquid and gas impermeable, odour permeable film of plastic material laminated to a web of paper.

The paper sheet (indicated by cross hatches) is located on the outer surface of the inner pouch walls 21a and 21b facing the outer pouch walls 2a and 2b, respectively.

The peelable sealing seams 22, 23 and 24 between the inner pouch walls 21a, 21b and the outer pouch walls 2a, 2b, respectively are provided by heat sealing whereby the plastic material of the outer pouch walls 2a and 2b melts and flows into the interstices of the paper sheet such that a bond is created between the films 2a and 2b and the paper sheet.

However, as the plastic material does not flow all the way through the paper sheet to fuse with the plastic material of the inner pouch walls 3a and 3b, respectively, the strength of the bond created by the heat sealing is dependent on the internal adherence forces between the fibres of the paper sheet and/or between the fibres and the films 2a, 2b and 3a, 3b.

By applying a peeling force transversely to the surface of the paper sheet, the bond can be broken manually so that the walls 2a and 3a and 2b and 3b can be separated by the manual peeling action described above for separating the outer pouch walls from the inner pouch for toilet disposal of the latter.

Alternatively, the outer pouch walls may be peelably adhered to the paper sheet by means of an adhesive having greater adhesion strength than the inner cohesion of the paper fibres. Finally, it is conceivable that the peelability of the seams be obtained by a relatively weak adhesion between, on the one hand, the outer pouch walls and/or the inner pouch walls and, on the other hand, the paper sheet so that the inner cohesion of the paper fibres is of less importance.

When peeling the peelable seams 8 and 9, the peeling force necessary for disrupting the peelable sealing seams will vary along the seams according to the width of the seam peeling front, i.e. the width of the seam in the direction at right angles to the peeling direction. Thus, the necessary peeling force will be largest when the peeling front is located at the top and bottom of the sealing seams 8 and 9 in for instance FIG. 8 and the necessary peeling force will be smallest when the peeling front of the seams 8 and 9 is located along the sides of the pouch.

The necessary peeling force should be such that the peeling force can easily be exerted by the user of the appliance without risk of ripping the outer pouch walls 2a and 2b and especially the inner pouch walls 3a and 3b when peeling. However, the necessary peeling force should also reflect attachment forces in the peelable seams 8 and 9 sufficient for ensuring the integrity of the appliance during use thereof.

It is currently believed that the necessary peeling force should be in the range of between approx. 0.5 Newton and approx. 6 Newton, preferably between approx. 0.7 Newton and approx. 5.5 Newton, even more preferably between approx. 0.8 Newton and approx. 5.0 Newton, even more preferably between approx. 0.9 Newton and approx. 4.5 Newton and most preferably between approx. 1.0 Newton and approx. 4.0 Newton.

The use of paper as the outer layer of the inner pouch double-layered walls affords further important advantages regarding the strength of the inner pouch, the feel and appearance of the inner pouch and the disposability of the inner pouch by being flushed through a toilet.

Water-disintegratable paper in dry condition has a relatively large tensile strength, and thus laminating paper on to a film of plastic material allows using a thinner film for achieving liquid and gas impermeability as well as sufficient combined strength.

This is advantageous from an economic viewpoint as less relatively expensive plastic material is required for the inner pouch walls.

Furthermore, when paper becomes wet, it loses some of its cohesion and tensile strength, and therefore the disposability of the inner pouch in a toilet is enhanced, as the decomposition of the inner pouch is facilitated because, firstly, the film is thinner and, secondly, because plastic material, even though it is a biodegradable plastic material, is relatively slow to disintegrate and biodegrade.

Finally, the user will be more comfortable throwing something feeling and looking like a paper or toilet tissue bag into the toilet than throwing a plastic bag into the toilet.

Paper types currently considered to be suitable for use in the inner pouch wall laminate are 100% cellulosic tissue paper of low wet strength such as Little Rapids Corp-Shawano Specialty Papers cellulose based paper Grade 3040 supplied by LRC-Shawano Specialty Papers, USA or paper including a binder such as Superseal Teabag Paper grade 478401 supplied by J.R. Crompton Ltd, UK.

In the context of the present invention, the term paper utilised in the specification and claims is to be understood to mean a non-woven fibrous web containing a substantial amount of cellulose fibres, preferably more than 30% by weight, more preferably more than 50% by weight, even more preferably more than 60% by weight and even more preferably more than 70% by weight, most preferably more than 95% by weight, and preferably without a binder for reasons of biodegradability.

Referring now to FIG. 6, the embodiment shown therein is identical to the embodiment of FIGS. 4-5 except for an additional peripheral heat sealing seam 25 of the inner pouch walls 21a and 21b to each other.

The purpose of this additional seam 25 is to safeguard against leakage of stomal discharge from the inner pouch if the peeling of the proximal outer pouch wall 2b from the distal inner pouch wall 21b or the peeling of the proximal inner pouch wall 21a from the proximal outer pouch wall 2a results in ripping of one or both of the inner pouch walls because of too forceful peeling or other reasons. The heat sealing seam 25 is shown spaced from the heat sealing seam 5, but they may be contiguous.

Referring now to FIG. 7, the embodiment shown therein is identical to the embodiment of FIGS. 1-3 except that the peelable sealing seam 26 corresponding to sealing seam 14 in FIGS. 1-3 is an annular film or textile with adhesive on both surfaces so that it adheres to both the inner pouch wall 3a and the outer pouch wall 2a, and that an annular insert 27 of cardboard is arranged as a tight fit against the inner surface 12a of the coupling ring 12.

The function of the annular insert 27 is to protect the inner surface 12a of the coupling ring 12 from contact with stomal discharge such that when disposing of the inner pouch in a toilet, the insert can be removed (for instance by being pressed out manually) and discarded in the toilet such that no part of the outer pouch and coupling ring is soiled by the stomal discharge and thus can be carried away in a pocket with no risk of bad odours and soiling of the pocket.

Protection of the inner surface of the coupling ring against being soiled by stomal discharge may also be achieved by peelably adhering an outwardly extending collar portion of the inner pouch wall 3a adjacent the coupling ring to said inner surface such that the collar will serve the same purpose as the insert 27, and upon removal of the inner pouch from the coupling ring will leave the coupling ring free of stomal discharge.

The releasable attachment of the pouch assembly comprising the inner pouch 3 and outer pouch 2 to the adhesive face plate assembly by means of the coupling rings 12 and 19 may be substituted by a releasable adhesive attachment of the outer pouch 2 and/or the inner pouch 3 to the carrier sheet 18 either directly or by means of releasable adhesion between an intermediate element attached to the carrier sheet 18 and/or the outer pouch 2 and/or the inner pouch 3 such that a new pouch assembly 2, 3 may be adhered to the face plate assembly 15 after removal and disposal of the previous pouch assembly.

Referring now to FIGS. 8-9, a one-piece ostomy appliance is shown, wherein the proximal outer pouch wall 2a is heat sealed to the carrier sheet 18 by means of an annular heat sealing seam 28 while the proximal inner pouch wall 3a is peelably sealed to the outer pouch wall 2a around the stoma receiving aperture by means of a peelable sealing seam 29 constituted by an annular film or textile with adhesive on both of its opposed surfaces.

At the top of the pouch the tongue 20 of the embodiment of FIGS. 1-3 has been substituted by three tongues 30, 31 and 32. The tongues are staggered and marked with the numerals 1, 2 and 3 to indicate the order in which they are to be gripped and pulled away, the tongue 32 being gripped first by one hand while gripping the tongue 31 with the other hand and pulling the tongue 32 away from the body of the user and so on until the desired separation of the appliance into two outer bag walls and the inner pouch has been accomplished.

Referring now to FIG. 10, this embodiment of a one-piece ostomy appliance according to the invention is very similar to the embodiment of FIGS. 8-9, but is provided with a lemon-like contour of the sealing seams 5, 6, 7, 8 and 9.

The object of this pointed contour is to facilitate the peeling separation of the peelable sealing seams 6 and 7 between the outer pouch walls 2a and 2b and the inner pouch walls 3a and 3b, respectively.

The pointed ends 33 and 34 act to concentrate the peeling forces and thus render it easier to initiate and end the peeling operation, respectively by presenting a small attachment area to start and end the peeling action.

The peelable sealing seam 35 between the inner pouch proximal wall and the outer pouch proximal wall around the stoma receiving apertures in these walls can either be round or have pointed ends 36 and 37 for facilitating the initiation and ending of the peeling operation on peelable sealing seam 35.

Referring now to FIG. 11, this embodiment is very similar to the embodiment of FIG. 4 except that the outer pouch film walls 2a and 2b and the comfort layers 4 have been extended beyond the periphery of the inner pouch walls 21a and 21b and an additional peelable sealing seam 38 has been provided for peelably joining the outer pouch walls together as a safety measure in case odours or flatus gasses wick through the fibres of the paper web laminated to the inner pouch film wall. In such case the additional sealing seam 38 will prevent the gasses and odours from exiting the outer pouch. Furthermore, this extra seam 38 will safeguard against water (for instance during showering) penetrating the fibres of the paper layer and reducing the sealing strength of the peelable sealing seems 22 and 23.

Referring now to FIG. 12, this embodiment is identical to the embodiment of FIG. 11 except that the peelable sealing seams 22 and 23 between the film walls 2a and 21a and 2b and 21b, respectively as well as the sealing seams 8 and 9 between the comfort layers and the film walls 2a and 2b, respectively, have been left out so that the inner pouch is only connected to the outer pouch by the peelable sealing seam 24 around the stoma receiving apertures. However, a peelable seal remains between the peripheral edges of the outer pouch walls 2a and 2b to allow such walls to be peeled apart and expose the inner pouch 3.

This embodiment has the same advantages as the FIG. 11 embodiment plus the advantage that the inner pouch 3 can be separated from the outer pouch 2 more easily and with less risk of rupturing the inner pouch during the separation.

Referring now to FIGS. 15 and 16, this currently preferred embodiment is similar to the embodiment shown in FIGS. 4-5. The inner and outer pouches 3 and 2 are symmetrical about a vertical axis of symmetry.

The paper sheet or any other suitable fibrous layer adhered or laminated to the outer surfaces of the inner pouch walls 3a and 3b may wick water present at the peripheral edge of the pouches 2 and 3, for instance when the user of the pouch assembly is bathing or showering, into the peelable seals 22 and 23 whereby the sealing strength thereof may be reduced to an extent that the seals 22 and 23 fail whereby the outer pouch walls 2a and 2b may become unintentionally separated from the inner pouch walls 3a and 3b.

To prevent this wicking from taking place, the outermost portion of the peripheral sealing seams 5, 8, 9, 22 and 23 is cut away along line 49 such that the heat generated by the cutting action melts and fuses the plastic material of outer and inner pouch walls 2a, 2b and 3a, 3b to create a seal along line 49 preventing water from coming into contact with the fibrous layers on the outer surfaces of the inner pouch walls 3a and 3b and thus preventing the wicking of water into the peelable seals 22 and 23.

The distal cover sheet 4 and the distal outer pouch wall 2b are cut away along cut lines 50 to expose a region 51b of the upper tab portion of the distal inner pouch wall 3b such that when initiating the peeling off of the outer pouch wall 2b with corresponding cover sheet 4, the user of the pouch assembly or a caregiver can grip the inner pouch tabs projecting above the cut lines 50 with one hand and grip the shortened tab portions below the cut lines 50 with the other hand and peel downwards in a manner very similar to the manner illustrated in FIG. 13.

So as to avoid wicking of water into the peelable seals 22 and 23 through the fibrous material attached to the outer surfaces of the tab portions 20c and 20d of the inner pouch walls 3b and 3a, respectively, heat is applied to areas 51a and 51b of the tab portions 20d and 20c, respectively, delimited by the peripheral edge of the tab portions and the dotted lines 52a and 52b, respectively, so as to melt the film material of the inner pouch walls in these areas so that the film material penetrates between the fibres of the fibrous material thereby reducing the wicking ability of the fibrous material.

As the areas 51b and 51a of the inner pouch tabs extend into the area of the peelable seams 22 and 23 thereby forming the areas 53a and 53b defined by the dotted lines 52a and 52b, these areas 53a and 53b are subjected to the heat sealing applied to form the peelable seals 22 and 23 whereby the wicking ability of the fibrous material is completely eliminated in the areas 53a and 53b because of further melting of the inner pouch wall film and melting of the outer pouch wall film whereby the interstices between the fibres in the fibrous material are substantially blocked and consequently no wicking path can be established for water inflow into the peelable seals 22 and 23.

It has turned out that for obtaining the best peel results the width of the peelable seals 22 and 23 should be between 4 and 6 mm, preferably approximately 5 mm, and that the width of the region in which heat and pressure is applied to form the peelable seal should be about 2 mm larger so that approx. 2 mm of the initial width of the peelable seals 22 and 23 is removed by the anti wicking cut along line 49.

Because of the symmetrical shape of the inner and outer pouches, the peeling action to peel off the distal outer pouch wall and the inner pouch takes place substantially parallel to the axis of symmetry and has turned out to require the least dexterity and force application to carry out the peeling action.

If the fibrous material attached to the outer surfaces of the inner pouch walls 3a and 3b is paper with a certain orientation of the cellulosic fibres, it has turned out that the orientation of the cellulosic fibres should be transverse to the peeling direction, i.e. in the case of the embodiment in FIGS. 15 and 16, transverse to the axis of symmetry, preferably substantially orthogonal to said axis. Hereby the best peeling result is obtained where most of the paper layer remains attached to the inner pouch walls after peeling of the peelable seams 22 and 23 has taken place.

All the features discussed in connection with the two-piece embodiments may be applied to the one-piece embodiments, and vice versa.

Furthermore, the insert 27 of FIG. 7, the triple tongues 30-32 of FIGS. 9 and 10, the paper/film laminate of the inner pouch walls of FIGS. 2, 5, 11 and 12, the double adhesive annular film 26 of FIGS. 7 and 9, the contours with pointed ends 33 and 34 and 36 and 37 of the sealing seams 6, 7 and 35, respectively, and the anti-wicking measures, the peeling seam width and the paper fibre orientation of FIGS. 15 and 16, may all be applied to the rest of the embodiments shown and described.

We claim:

1. An ostomy appliance for receiving discharge from a human stoma and comprising:
   attachment means for attaching the appliance to the peristomal skin surface of a user of the appliance, and
   an ostomy pouch assembly comprising:
   an inner pouch attached to said attachment means and having a first aperture for receiving the stoma of said user,
   said inner pouch being defined by a flexible body side or proximal inner pouch wall and a flexible distal inner pouch wall, and one or more peripherally extending inner pouch sealing seams,
   an outer pouch enclosing said inner pouch, attached to said attachment means and having a second aperture for receiving said stoma and being aligned with said first aperture,
   said outer pouch being defined by a flexible body side or proximal outer pouch wall and a flexible distal outer pouch wall, and one or more peripherally extending outer pouch sealing seams,
   said one or more outer pouch sealing seams being manually peelable such that the attachment forces provided by said one or more outer pouch sealing seams may be manually eliminated by manually pulling said distal outer pouch wall in a direction transverse to said one or more peelable outer pouch sealing seams,
   said one or more outer pouch sealing seams peelably attaching said distal outer pouch wall to said distal inner pouch wall and said proximal outer pouch wall to said proximal inner pouch wall.

2. An ostomy appliance according to claim 1, wherein said inner pouch is attached to said attachment means by a peelable interior sealing seam extending around said stoma receiving aperture in said inner pouch.

3. An ostomy appliance according to claim 2, wherein the material of said inner pouch walls is biodegradable.

4. An ostomy appliance according to claim 2, wherein said interior inner pouch sealing seam comprises a peeling action initiation zone, where the interior inner pouch sealing seam comprises a peak-like extent tapering in the direction opposite a predetermined peeling direction.

5. An ostomy appliance according to claim 1, wherein said inner pouch walls are made of a plastic film laminated to a web of tissue paper, said web facing outwards relative to the interior of said inner pouch.

6. An ostomy appliance according to claim 5, wherein said tissue paper and said plastic film are biodegradable.

7. An ostomy appliance according to claim 5, wherein said outer pouch peelable seam is made by applying heat and/or RE to the outer surface of one or both of said outer pouch walls.

8. An ostomy appliance according to claim 1, wherein said inner pouch walls are impermeable to liquid and gas and permeable to odors, and said outer pouch walls are impermeable to liquid, gas and odors.

9. An ostomy appliance according to claim 1, wherein said one or more outer pouch peeling seams comprises a peeling action initiation zone, where said one or more outer pouch sealing seams comprises a peak-like extent tapering in the direction opposite a predetermined peeling direction.

10. An ostomy appliance according to claim 1, wherein said one or more outer pouch peeling seams comprises a peeling action ending zone, where said one or more outer pouch sealing seams comprises a peak-like extent tapering in a predetermined peeling direction.

11. An ostomy appliance according to claim 1, wherein said proximal outer pouch wall is attached to said attachment means by a heat sealed sealing seam.

12. An ostomy appliance according to claim 1, wherein said proximal outer pouch wall is attached to said attachment means by a peelable sealing seam.

13. An ostomy appliance according to claim 1, wherein said attachment means comprises a face plate assembly comprising a wafer of skin friendly adhesive material having a third aperture for receiving said stoma aligned with said first and second apertures, and a first coupling ring surrounding said third aperture and attached to said wafer and in engagement with a second coupling ring surrounding said first and second apertures and attached to said proximal outer pouch wall and/or to said proximal inner pouch wall.

14. An ostomy appliance according to claim 13, wherein said proximal outer pouch wall is attached to said second coupling ring by means of a heat sealed sealing seam.

15. An ostomy appliance according to claim 13 or 14, wherein said proximal inner pouch wall is attached to said second coupling ring by means of said peelable interior sealing seam.

16. An ostomy appliance according to claim 13 or 14, wherein said proximal inner pouch wall is attached to said proximal outer pouch wall in a region surrounding said first and second apertures by means of said peelable interior sealing seam.

17. An ostomy appliance according to claim 1, wherein said attachment means comprises a face plate assembly comprising a wafer of skin friendly adhesive material having a third aperture for receiving said stoma aligned with said first and second apertures, and a first coupling means surrounding said third aperture and attached to said wafer and in releasably adhesive engagement with a second coupling means surrounding said first and second apertures and attached to said proximal outer pouch wall and/or to said proximal inner pouch wall.

18. An ostomy appliance according to claim 17, wherein said proximal outer pouch wall is attached to said second coupling means by means of a heat sealed sealing seam.

19. An ostomy appliance according to claim 17 or 18, wherein said proximal inner pouch wall is attached to said second coupling means by means of said peelable interior sealing seam.

20. An ostomy appliance according to claim 17 or 18, wherein said proximal inner pouch wall is attached to said proximal outer pouch wall in a region surrounding said first and second apertures by means of said peelable interior sealing seam.

21. An ostomy appliance according to claim 1, wherein said attachment means comprises a face plate assembly comprising a wafer of skin friendly adhesive material having a fourth aperture for receiving said stoma aligned with said first and second apertures, and a carrier sheet attached to the distal surface of said wafer and attached to said proximal outer pouch wall and to said proximal inner pouch wall.

22. An ostomy appliance according to claim 21, wherein said proximal outer pouch wall is attached to said carrier sheet by means of a heat sealed sealing seam.

23. An ostomy appliance according to claim 21 or 22, wherein said proximal inner pouch wall is attached to said carrier sheet by means of said interior peelable sealing seam.

24. An ostomy appliance according to claim 21 or 22, wherein said proximal inner pouch wall is attached to said proximal outer pouch wall in a region surrounding said first and second apertures by means of said peelable interior sealing seam.

25. An ostomy appliance according to claim 1, wherein said attachment forces provided by said one or more peelable outer pouch sealing seams are such that the pulling force required for manually overcoming said attachment forces is between approximately 0.5 Newton and approximately 6 Newton.

26. An ostomy appliance according to claim 25, wherein said outer pouch peelable sealing seams are between 4 and 6 mm wide.

27. An ostomy appliance according to claim 25 wherein said pulling force is between approximately 1.0 Newton and approximately 4.0 Newton.

28. An ostomy appliance according to claim 26 wherein said outer pouch sealing seams are approximately 5 mm wide.

29. An ostomy appliance according to claim 1, wherein at least a portion of the outer peripheral edges of said outer pouch wall and said inner pouch wall has been formed by cutting through both of said walls in the areas of said outer pouch peelable seams.

30. An ostomy appliance for receiving discharge from a human stoma and comprising:
    attachment means for attaching the appliance to the peristomal skin surface of a user of the appliance, and
    an ostomy pouch assembly comprising:
    an inner pouch attached to said attachment means and having a first aperture for receiving the stoma of said user,
    said inner pouch being defined by a flexible body side or proximal inner pouch wall and a flexible distal inner pouch wall, and one or more peripherally extending inner pouch sealing seams,
    an outer pouch enclosing said inner pouch, attached to said attachment means and having a second aperture for receiving said stoma and being aligned with said first aperture,
    said outer pouch being defined by a flexible body side or proximal outer pouch wall and a flexible distal outer pouch wall, and one or more peripherally extending outer pouch sealing seams,
    said one or more outer pouch sealing seams being manually peelable such that the attachment forces provided by said one or more peelable outer pouch sealing seams may be overcome by manually pulling said distal outer pouch wall in a direction transverse to said one or more peelable outer pouch sealing seams,
    wherein said inner pouch is attached to said attachment means by a peelable interior sealing seam extending around said stoma receiving aperture in said inner pouch, and
    wherein said interior inner pouch sealing seam comprises a peeling action ending zone, where the interior inner pouch sealing seam comprises a peak-like extent tapering in a predetermined peeling direction.

31. An ostomy appliance for receiving discharge from a human stoma and comprising:
    attachment means for attaching the appliance to the peristomal skin surface of a user of the appliance, and
    an ostomy pouch assembly comprising:
    an inner pouch attached to said attachment means and having a first aperture for receiving the stoma of said user,
    said inner pouch being defined by a flexible body side or proximal inner pouch wall and a flexible distal inner pouch wall, and one or more peripherally extending inner pouch sealing seams,
    an outer pouch enclosing said inner pouch, attached to said attachment means and having a second aperture for receiving said stoma and being aligned with said first aperture,
    said outer pouch being defined by a flexible body side or proximal outer pouch wall and a flexible distal outer pouch wall, and one or more peripherally extending outer pouch sealing seams,
    said one or more outer pouch sealing seams being manually peelable such that the attachment forces provided by said one or more peelable outer pouch sealing seams may be overcome by manually pulling said distal outer pouch wall in a direction transverse to said one or more peelable outer pouch sealing seams,
    said inner pouch being attached to said attachment means by a peelable interior sealing seam extending around said stoma receiving aperture in said inner pouch,
    wherein said peelable interior sealing seam is constituted by a sheet of film or textile with a fifth stoma receiving aperture and having adhesive on both opposed surfaces.

32. An ostomy appliance for receiving discharge from a human stoma and comprising:
    attachment means for attaching the appliance to the peristomal skin surface of a user of the appliance, and
    an ostomy pouch assembly comprising:
    an inner pouch attached to said attachment means and having a first aperture for receiving the stoma of said user,
    said inner pouch being defined by a flexible body side or proximal inner pouch wall and a flexible distal inner pouch wall, and one or more peripherally extending inner pouch sealing seams,
    an outer pouch enclosing said inner pouch, attached to said attachment means and having a second aperture for receiving said stoma and being aligned with said first aperture,
    said outer pouch being defined by a flexible body side or proximal outer pouch wall and a flexible distal outer pouch wall, and one or more peripherally extending outer pouch sealing seams, said one or more outer pouch sealing seams being manually peelable such that the attachment forces provided by said one or more peelable outer pouch sealing seams may be overcome by manually pulling said distal outer pouch wall in a direction transverse to said one or more peelable outer pouch sealing seams, wherein said attachment means comprises a face plate assembly comprising a wafer of skin friendly adhesive material having a third aperture for receiving said stoma aligned with said first and second apertures, a first coupling ring surrounding said third aperture and attached to said wafer and in releasable adhesive engagement with a second coupling ring surrounding said first and second apertures and attached to said proximal outer pouch wall and/or to said proximal inner pouch wall, wherein an annular insert having a sixth aperture for receiving said stoma is provided within said second coupling ring for preventing said stomal discharge from soiling said second coupling ring.

33. An ostomy appliance for receiving discharge from a human stoma and comprising:

attachment means for attaching the appliance to the peristomal skin surface of a user of the appliance, and an ostomy pouch assembly comprising:

an inner pouch attached to said attachment means and having a first aperture for receiving the stoma of said user, said inner pouch being defined by a flexible body side or proximal inner pouch wall and a flexible distal inner pouch wall, and one or more peripherally extending inner pouch sealing seams, an outer pouch enclosing said inner pouch, attached to said attachment means and having a second aperture for receiving said stoma and being aligned with said first aperture, said outer pouch being defined by a flexible body side or proximal outer pouch wall and a flexible distal outer pouch wall, and one or more peripherally extending outer pouch sealing seams, said one or more outer pouch sealing seams being manually peelable such that the attachment forces provided by said one or more outer pouch sealing seams may be manually eliminated by manually pulling said distal outer pouch wall in a direction transverse to said one or more peelable outer pouch sealing seams, a portion of said outer pouch walls and inner pouch walls extending beyond said outer pouch peelable seams to form inner pouch wall and outer pouch wall gripping tabs for peeling said walls apart.

34. An ostomy pouch according to claim 33, wherein an area of each of said inner pouch wall gripping tabs extending into the area covered by the adjacent outer pouch peelable seam has been subjected to application of heat and/or RF prior to the formation of said outer pouch peelable seams.

35. An ostomy appliance for receiving discharge from a human stoma and comprising:

attachment means for attaching the appliance to the peristomal skin surface of a user of the appliance, and an ostomy pouch assembly comprising:

an inner pouch attached to said attachment means and having a first aperture for receiving the stoma of said user, said inner pouch being defined by a flexible body side or proximal inner pouch wall and a flexible distal inner pouch wall, and one or more peripherally extending inner pouch sealing seams, an outer pouch enclosing said inner pouch, attached to said attachment means and having a second aperture for receiving said stoma and being aligned with said first aperture, said outer pouch being defined by a flexible body side or proximal outer pouch wall and a flexible distal outer pouch wall, and one or more peripherally extending outer pouch sealing seams, said one or more outer pouch sealing seams being manually peelable such that the attachment forces provided by said one or more peelable outer pouch sealing seams may be overcome by manually pulling said distal outer pouch wall in a direction transverse to said one or more peelable outer pouch sealing seams, said inner pouch walls being made of a plastic film laminated to a web of tissue paper, said web facing outwards relative to the interior of said inner pouch, wherein a significant portion of the fibers of said tissue paper have a generally uniform orientation and said orientation is transversal to a line extending from the top to the bottom of said outer and inner pouches when a user to said pouches have been applied around a stoma is standing erect, said orientation being generally orthogonal to said line.

* * * * *

UNITED STATES PATENT AND TRADEMARK OFFICE
CERTIFICATE OF CORRECTION

PATENT NO.        : 7,517,339 B2
APPLICATION NO.   : 10/969523
DATED             : April 14, 2009
INVENTOR(S)       : Ole Pedersen et al.

It is certified that error appears in the above-identified patent and that said Letters Patent is hereby corrected as shown below:

On the Title Page:

At Item (75), second named Inventor, "Forbjerg-Iarsen" should be -- Forbjerg-larsen --.

In the Claims:

At Column 14, line 9, "RE" should be -- RF --.

Signed and Sealed this

Ninth Day of March, 2010

David J. Kappos
*Director of the United States Patent and Trademark Office*